United States Patent [19]

Harfenist et al.

[11] Patent Number: 4,737,514

[45] Date of Patent: Apr. 12, 1988

[54] METHOD FOR TREATING DEPRESSION WITH THIOXANTHEN-9-ONE DERIVATIVES

[75] Inventors: Morton Harfenist, Chapel Hill; Charles T. Joyner; Darryl J. Heuser, both of Raleigh, all of N.C.

[73] Assignee: Burroughs Wellcome Co., Research Triangle Park, N.C.

[21] Appl. No.: 817,752

[22] Filed: Jan. 2, 1986

Related U.S. Application Data

[62] Division of Ser. No. 688,747, Jan. 4, 1985, abandoned.

[30] Foreign Application Priority Data

May 1, 1984 [GB] United Kingdom ............... 8400203

[51] Int. Cl.$^4$ ................ A61K 31/38; A61K 31/535
[52] U.S. Cl. .................... 514/437; 514/227; 514/397; 544/336; 544/145; 549/27
[58] Field of Search ............ 544/336, 145; 549/27; 514/227, 397, 437

[56] References Cited

U.S. PATENT DOCUMENTS

| 3,310,553 | 3/1967 | Bloom et al. | 549/27 |
| 3,642,997 | 2/1972 | Shen et al. | 549/27 |
| 4,177,257 | 12/1979 | Hodson et al. | 549/27 |

FOREIGN PATENT DOCUMENTS 1458185 12/1976 United Kingdom ............... 549/27

OTHER PUBLICATIONS

Sheehan, J. Psychiatry, 45, 1984, pp. 29-36.

Primary Examiner—Henry R. Jiles
Assistant Examiner—J. G. Mullins
Attorney, Agent, or Firm—Donald Brown

[57] ABSTRACT

Compounds of formula (I)

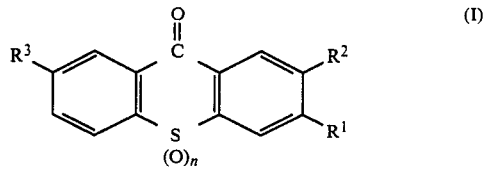

wherein n is 0, 1 or 2;

one or $R^1$ and $R^2$ is hydrogen and the other is selected from carbamoyl, N-$C_{1-4}$alkylcarbamoyl, N,N-di-$C_{1-4}$alkylcarbamoyl, carbamimidoyl, $N^1$-$C_{1-4}$ alkylcarbamimidoyl, $N^2$-$C_{1-4}$ alkylcarbamimidoyl, $N^1$-$C_{1-4}$alkyl-$N^2$-$C_{1-4}$ alkylcarbamimidoyl, $N^1,N^1$-di-$C_{1-4}$ alkylcarbamimidoyl, $N^1,N^1$-di-$C_{1-4}$alkyl-$N^2$-$C_{1-4}$ alkylcarbamimidoyl and imidazolin-2-yl (optionally substituted by one or more $C_{1-4}$ alkyl groups); and $R^3$ is selected from hydrogen, saturated and unsaturated aliphatic hydocarbon moieties containing from 1 to 4 carbon atoms, groups $OR^4$ (where $R^4$ is selected from hydrogen and saturated and unsaturated aliphatic hydrocarbon moieties containing from 1 to 4 carbon atoms), halo, groups of formula—$NR^5R^6$ (where $R^5$ and $R^6$ are independently selected from hydrogen, $C_{1-4}$ alkyl and hydroxy $C_{1-4}$ alkyl, provided that the total number of carbon atoms in $R^5$ and $R^6$ does not exceed 4), amino $C_{1-4}$ alkylamino and morpholino, provided that when n is 2 and $R^2$ is hydrogen, then $R^1$ is not carbamoyl when $R^3$ is hydrogen or methyl; and $R^1$ is not N-methylcarbamoyl when $R^3$ is hydrogen; and physiologically acceptable salts thereof, and their pro-drugs and metabolites are inhibitors of monoamine oxidase-A and are useful in the prophylaxis and treatment of mental disorders such as depression.

2 Claims, No Drawings

METHOD FOR TREATING DEPRESSION WITH THIOXANTHEN-9-ONE DERIVATIVES

This application is a division of application Ser. No. 688,747, filed Jan. 4, 1985, now abandoned.

The present invention relates to tricyclic compounds having valuable monoamine oxidase inhibitory activity.

Monoamine oxidase (MAO) is a brain enzyme believed to be responsible for intraneuronal catalysis of oxidation of biogenic amine neurotransmitters to inactive forms. It is understood to occur as two independent enzymes normally designated MAO-A and MAO-B (White and Glassman, J. Neurochem., 29, 989–997, (1977) and Tipton et al, "Monoamine Oxidase and its Selective Inhibitors", Beckmann and Riederer, Eds., Mod. Probl. Pharmacopsychiat., 19 15–30, Karger, Basel (1983)). MAO inhibition has been found to elevate neurotransmitter concentration in the brain. MAO inhibitors are used therapeutically in the treatment of a wide variety of conditions, especially depression, particularly when characterized by anxiety obessional neuroses, or appetite disorders.

We have now discovered that thioxanthen-9-one derivatives of formula (I) possess advantageous MAO-A inhibitory properties which render the compounds useful for the treatment of mental and other disorders.

The present invention thus provides a compound of formula (I)

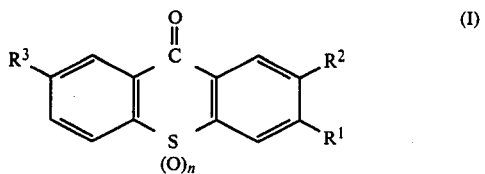

wherein
n is 0, 1 or 2;
one of $R^1$ and $R^2$ is hydrogen and the other is selected from, N-$C_{1-4}$alkylcarbamoyl, N,N-di-$C_{1-4}$alkylcarbamimidoyl, carbamimidoyl, $N^1$-$C_{1-4}$alkylcarbamimidoyl, $N^2$-$C_{1-4}$alkylcarbamimidoyl, $N^1$-$C_{1-4}$alkyl-$N^2$-$C_{1-4}$alkylcarbamimidoyl, $N^1,N^1$-di-$C_{1-4}$alkylcarbamimidoly, $N^1,N^1$-di-$C_{1-4}$alkyl-$N^2$-$C_{1-4}$alkylcarbamimidoyl and imidazolin-2-yl (optionally substituted by one or more $C_{1-4}$alkyl groups); and
$R^3$ is selected from hydrogen, saturated and unsaturated aliphatic hydrocarbon moieties containing from 1 to 4 carbon atoms, groups $OR^4$ (wherein $R^4$ is selected from hydrogen and saturated and unsaturated aliphatic hydrocarbon moieties containing from 1 to 4 carbon atoms), halo groups of formula—$NR^5R^6$ (where $R^5$ and $R^6$ are independently selected from hydrogen, $C_{1-4}$alkyl and hydroxy-$C_{1-4}$alkyl, provided that the total number of carbon atoms in $R^5$ and $R^6$ does not exceed 4), amino-$C_{1-4}$alkylamino and morpholino;
provided that when n is 2 and $R^2$ is hydrogen, then $R^1$ is not carbamoyl when $R^3$ is hydrogen or methyl; and
$R^1$ is not N-methylcarbamoyl when $R^3$ is hydrogen.

Included within the scope of the compounds of formula (I) are the physiologically acceptable salts of such compounds. In particular, these may be the acid addition salts of those compounds wherein one of $R^1$ and $R^2$ represents a carbamimidoyl, $N^1$-$C_{1-4}$alkylcarbamimidoyl, $N^2$-$C_{1-4}$alkylcarbamimidoyl, $N^1$-$C_{1-4}$-alkyl-$N^2$-$C_{1-4}$-alkylcarbamimidoyl, $N^1,N^1$-di-$C_{1-4}$alkylcarbamimidoyl, $N^1,N^1$-di-$C_{1-4}$alkyl-$N^2$-$C_{1-4}$alkylcarbamimidoyl or/an optionally alkylated imidazolin-2-yl group and/or $R^3$ represents a group of formula —$NR^5R^6$, an amino —$C_{1-4}$alklamino group or a morpholino group, for example those derived from hydrochloric, hydrobromic, phosphoric, malic, maleic, fumaric, citric, sulphuric, lactic and tartaric acids.

In formula (I) when $R^3$ and/or $R^4$ is a saturated or unsaturated $C_{1-4}$aliphatic hydrocarbon moiety, these groups may be selected independently from, for example $C_{1-4}$alkyl, $C_{2-4}$alkenyl and $C_{2-4}$alkynyl groups.

A preferred subclass of the compounds of formula (I) comprises those compounds wherein $R^1$ is hydrogen, $R^2$ represents an imidazolin-2-yl group and $R^3$ represents a group selected from $C_{1-4}$alkyl (especially isopropyl), mono-or di-$C_{1-4}$alkylamino and morpholino; and physiologically acceptable salts thereof. Other subclasses of compounds of formula (I) and their physiologically acceptable salts include those wherein:
(i) $R^1$ is hydrogen;
(ii) $R^2$ is hydrogen; and
(iii) one of $R^1$ and $R^2$ is hydrogen and the other is selected from carbamoyl, N-$C_{1-4}$alkylcarbamoyl, carbamimidoyl, $N^1$-$C_{1-4}$alkylcarbamimidoyl and imidazolin-2-yl; and
$R^3$ is selected from hydrogen, saturated and unsaturated aliphatic hydrocarbon moieties containing from 1 to 4 carbon atoms, groups $OR^4$ (wherein $R^4$ is selected from hydrogen and saturated and unsaturated aliphatic hydrocarbon moieties containing from 1 to 4 carbon atoms), halo, groups of formula —$NR^5R^6$ (where $R^5$ and $R^6$ are independently selected from $C_{1-4}$alkyl and hydroxy-$C_{1-4}$alkyl, provided that the total number of carbon atoms in $R^5$ and $R^6$ does not exceed 4), amino $C_{1-4}$alkylamino and morpholino.

Particularly preferred compounds of formula (I) include the following compounds and where appropriate their physiologically acceptable salts, especially their hydrochlorides and dihydrochlorides;

A. 3-(2-Imidazolin-2-yl)thioxanthen-9-one 10,10-dioxide
B. 6-(2-Imidazolin-2-yl)-2-methoxythioxanthen-9-one, 10,10-dioxide
C. 2-Ethoxy-6-(2-imidazolin-2-yl)thioxanthen-9-one 10,10-dioxide
D. 6-(2-Imidazolin-2-yl)-2-propoxythioxanthen-9-one, 10,10-dioxide
E. 6-(2-Imidazolin-2-yl)-2-fluorothioxanthen-9-one 10,10-dioxide
F. 6-(2-Imidazolin-2-yl)-2-methylthioxanthen-9-one 10,10-dioxide
G. 6-(2-Imidazolin-2-yl)-2-propylthioxanthen-9-one 10,10-dioxide
H. 6-(2-Imidazolin-2-yl)-2-isopropylthioxanthen-9-one 10,10-dioxide
I. 2-Ethylamino-6-(2-imidazolin-2-yl)thioxanthen-9-one 10,10-dioxide
J. 2-Dimethylamino-6-(2-imidazolin-2-yl)thioxanthen-9-one 10,10-dioxide
K. 6-(2-Imidazolin-2-yl)-2-(propylamino)thioxanthen-9-one 10,10-dioxide
L. 2-(N-Ethylmethylamino)-6-(2-imidazolin-2-yl)thioxanthen-9-one 10,10-dioxide
M. 2-Allylamino-6-(2-imidazolin-2-yl)thioxanthene-9-one 10,10-dioxide N. 2-(2-Aminoethylamino)-6-(2-imidazolin-2-yl)thioxanthen-9-one 10,10-dioxide
O. 6-(2-Imidazolin-2-yl)-2-morpholinothioxanthen-9-one 10,10-dioxide
P. 2-Chloro-6-(2-imidazolin-2yl)thioxanthen-9-one, 10,10-dioxide
Q. 6-N-Ethylcarbamoyl-2-propoxythioxanthen-9-one 10,10-dioxide
R. 2-Isopropyl-6-methylcarbamoylthioxanthen-9-one 10,10-dioxide This invention further includes a method of inhibiting monoamine oxidase-A (MAO-A) in mammals including humans. This method comprising administration to a mammal which has been identified as being in need of inhibition of MAO-A of a compound of formula (I) or, where possible, a physiologically acceptable salt thereof in an amount sufficient to inhibit MAO-A.

This invention also includes a method of prophylaxis or treatment of a mental disorder in mammals, primarily humans. This method comprises administration to the mammal of a therapeutically effective amount of a compound of formula (I) or a physiologically acceptable salt thereof.

In such a method the mental disorder may for example be:
(a) depression, particularly that characterized by anxiety or obsessional neuroses, or an atypical depression, e.g., accompanied by a personality disorder;
(b) obsessive compulsive states;
(c) anxiety states, e.g., which are accompanied in an acute phase by panic attacks;
(d) certain appetite disorders, e.g., bulimia and anorexia.

Compounds of formula (I) and their physiologically acceptable salts may be administered, for example, by the oral, rectal or parenteral route. In general, the compound, may be administered at a dosage in the range of 1 mg to 100 mg per kg of recipient bodyweight per day, although the precise dosage will naturally depend on a number of clinical factors, for example, the type (i.e., human or other animal), age of the recipient, the condition under treatment and its severity. For administration of the compounds by the oral route, a dosage regime of 1 to 50 mg per kg per day preferably 10 to 40, e.g., about 25 mg per kg per day may be used. For administration by the parenteral route, a dosage regime of 0.2 to 10 mg per kg per day, advantageously 1 to 5 mg per kg per day, e.g., about 2 mg per kg per day is generally preferred.

While it is possible to administer compounds of formula (I) as raw compounds, it is highly desirable to administer them in the form of a pharmaceutical formulation.

The present invention thus further provides pharmaceutically acceptable formulations comprising as active ingredient, one or more compounds of formula (I) (as defined above) or physiologically acceptable salt(s) thereof, or pro-drugs thereof in association with at least one pharmaceutical carrier or excipient. The pharmaceutical formulations may be adapted for oral, parenteral or rectal administration.

The formulations may conveniently be presented in unit dosage form and may be prepared by any of the methods well known in the art of pharmacy. Such methods include the step of bringing into association the active ingredient with the carrier which may comprise one or more accessory ingredients. In general the formulations are prepared by uniformly and intimately bringing into association the active ingredient with liquid carriers or finely divided solid carriers or both, and the, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid or as an oil-in-water liquid emulsion or a water-in-oil liquid emulsion.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or control release of the active ingredient therein.

Formulations for rectal administration may be presented as a suppository with the usual carriers such as cocoa butter.

Formulations suitable for parenteral administration include aqueous sterile injection solutions which may contain antioxidants, buffers, bacteriostats and solutes which render the formulation isotonic with the blood of the intended recipient; and aqueous and nonaqueous sterile suspensions which may include suspending agents and thickening agents. The formulations may be presented in unitdose or multidose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powder, granules and tablets of the kind previously described.

Preferred unit dosage formulations are those containing a daily dose or unit daily subdose, as hereinabove recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

The compounds of formula (I) and their physiologically acceptable salts may be synthesized by any method known in the art for synthesis of compounds of like and analogous structure, for example as described in the Batchelor and Hodson specifications, and in particular by the processes described hereinbelow.

Thus, according to a further feature of the present invention we provide a process for the preparation of compounds of formula (I) (as hereinbefore defined) and their physiologically acceptable salts, the said process comprising:
(a) reacting a compound of formula (II)

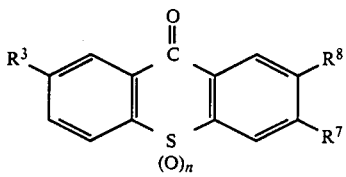

(wherein $R^3$ and n are as previously defined, and one of $R^7$ and $R^8$ is hydrogen and the other is a precursor for a group $R^1$ or $R^2$ respectively, as hereinbefore defined) with an agent or agents serving to effect conversion of the $R^7$ or $R^8$ group to the desired $R^1$ to $R^2$ group as appropriate; or (b) oxidising a compound of formula (III)

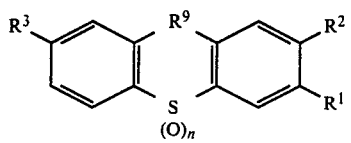

(wherein $R^1$–$R^3$ and n are as defined above and $R^9$ is a methylene group or a group of formula

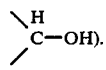

Where appropriate, in either of processes (a) or (b) above, the reactant compound of formula (II) or (III) may be provided in the form of a suitable salt thereof. The above processes, where appropriate, may also include one or more of the following optional steps:

(i) Converting the resultant compound of formula (I) salt thereof, or a precursor therefor, into a physiologically acceptable salt thereof.

(ii) Where the group $R^3$ in the resultant compound of formula (I) is a displaceable group, for example a halogen such as fluorine, converting the compound to another compound of formula (I) wherein $R^3$ is a group $OR^4$ or $-NR^5R^6$ as defined, or an amino-$C_{1-4}$alkylamino group, by reaction with an appropriate alkoxide or amino compound, for example $NaOCH_3$ or $HN(CH_3)$ in a suitable solvent, e.g. methanol or dimethylformamide (DMF) preferably in the presence of a base. It will be appreciated that similar displacements may also be performed at various stages of the preparation of compounds of formula (I).

(iii) At an appropriate point in a synthetic route to a compound of formula (I), protecting one or more functional groups (for example, converting the central carbonyl group to a ketal group) and in a later or final step, deprotecting in order to regenerate the desired group.

(iv) Where, in a compound of formula (I) or a physiologically acceptable salt thereof, n is 0 or 1, increasing the oxidation state of the sulphur atom so as to form respectively, a corresponding compound or salt wherein n is 1 or 2, or 2. Again, it will be appreciated that oxidation of the sulphur atom may be performed at any appropriate stage of the preparation.

(v) Where, in a compound of formula (I) or a physiologically acceptable salt thereof, $R^1$ or $R^2$ represents an unsubstituted carbamoyl or carbamimidoyl group, alkylating the said group to form a corresponding compound wherein $R^1$ or $R^2$ as appropriate, represents either an N-$C_{1-4}$alkylcarbamoyl, N,N-di-$C_{1-4}$alkylcarbamoyl, $N^1$-$C_{1-4}$alkylcarbamimidoyl, $N^2$-$C_{1-4}$alkylcarbamimidoyl, $N^1$-$C_{1-4}$alkyl-$N^2$-$C_{1-4}$alkylcarbamimidoyl $N^1,N^1$-di-$C_{1-4}$alkylcarbamimidoyl, or $N^1,N^1$-di-$C_{1-4}$alkyl-$N^2$-$C_{1-4}$alkylcarbamimidoyl group. Such alkylation may also be performed at any appropriate stage of synthesis. The alkylation may be performed by any of methods well known to those skilled in the art, for example by reaction with an alkyl-(eg. methyl-)halide, for example the iodide.

For the preparation of compounds of formula (I') wherein one of $R^1$ and $R^2$ is hydrogen and the other is a carbamoyl, N-$C_{1-4}$alkylcarbamol or N,N-di-$C_{1-4}$alkylcarbamoyl group, process (a) above may comprise reaction of a compound of formula (II) wherein one of $R^7$ and $R^8$ is hydrogen and the other is an appropriate carbonyl derivative with one or more suitable reagents serving to effect amination of the said carbonyl derivative. Thus for example, where the $R^7$ or $R^8$ group represents an activated carbonyl group such as an ester or an acid chloride, the compound of formula (II) may be reacted with ammonia or a corresponding alkyl-or dialkylamine, for example methylamine, preferably under aqueous conditions. If the carbonyl derivative is carboxy, the compound of formula (II) may be treated with a reagent serving to effect formation of a corresponding activated acid, in the presence of, or followed by reaction with an appropriate reagent such as described above in respect of reactions with esters and acid chlorides.

The reagent serving to effect formation of a corresponding activated acid or derivative may be a sulfur oxychloride such as thionyl chloride, a phosphorus halide such as phosphorus tri- or pentachloride, a phosphorus oxyhalide such as the oxychloride, trifluoroacetic anhydride, an alkyl- (e.g., ethyl-) chloroformate or any other suitable agent which will be apparent to those skilled in the art. A list of such reagents appears in Methoden der organischen Chemie, Houben-Weyl, 4th Edn., Vol 15, 1, p. 29. Conveniently, the reaction may be performed in a suitable solvent such as toluene, desirably in the presence of an appropriate catalyst such as dimethylformamide. Alternatively the reaction may be effected by reaction with an appropriate weak or volatile base such as methylamine, preferably by heating. Such a reaction conveniently may be effected using a stream of methylamine or by use of methylamine in situ in the presence of a dehydrating agent.

For the preparation of compounds of formula (I') wherein one of $R^1$ and $R^2$ is hydrogen and the other is a carbamimidoyl, $N^1$-$C_{1-4}$alkylcarbamimidoyl, $N^2$-$C_{1-4}$alkylcarbamimidoyl, $N^1$-$C_{1-4}$alkyl-$N^2$-$C_{1-4}$alkylcarbamimidoyl, $N^1,N^1$-di-$C_{1-4}$alkylcarbamimidoyl, $N^1,N^1$-di-$C_{1-4}$alkyl-$N^2$-$C_{1-4}$alkylcarbamimidoyl, or optionally alkylated imidazolin-2-yl group, the precursor group may be a cyano group.

In processes (b), the oxidation may be effected by reaction with hydrogen peroxide in acetic acid, with an organic peracid such as meta-chlorobenzoic acid in an inert solvent, e.g., chloroform or dichloromethane, or with an inorganic peracid. Alternative oxidising agents for use in this stage of the process including ozone and alkali metal permanganates. Where the reaction is performed in an organic solvent, a crown ether is preferably included to ensure solution of the reagent. Other suitable inorganic oxidising agents include alkali metal chromates and dichromates in an unreactive solvent such as acetic acid. When it is also desired to perform the sulfur oxidation of option (iv) above and this is not brought about simultaneously with the oxidation of the 9-OH group in process (b), then it may be effected by admixture with a catalytic amount of strong base such as an alkali metal hydroxide or alkoxide, e.g. the t-butoxide, thereby promoting the air oxidation.

The compounds of formulae (III) and (IV) and their salts may be prepared by processes analogous to those described in the Hodson and Batchelor specifications and also in U.S. Pat. Nos. 4,012,499; 4,025,635; 4,103,015; 4,145,350; and 4,177,257.

The compounds of formula (II) may be prepared from compounds of formula (III) by any of the conventional methods known in the art, for example hydrolysis followed by either treatment with sulphur oxychloride or esterification. The following examples illustrate the present invention.

EXAMPLE 1

Reference
Preparation-3-N-methylcarbamoylthioxanthen-9-one 10,10-dioxide

To 345.2 g (1.2 mol) or 3-carboxy-10,10-dioxothioxanthone was added 1.5 Kg $SOCL_2$ and the mixture was refluxed overnight to convert the 3-carboxy group to the corresponding 3-carbonyl chloride, i.e., acid chloride. A further 500 g of $SOCL_2$ was added and reflux was continued for another day. Excess $SOCL_2$ was removed under vacuum (water aspirator). The residue was cautiously added with cooling and stirring to 1500 g of cold 70% aq. $NH_2CH_3$ and was stirred for 2 days. The precipitate was filtered, washed with aq. $NaHCO_3$ and dried to leave a solid residue, weight 328 g. The procedure was repeated using another 200 g of acid starting material.

The resultant solids were washed in $NaHCO_3$ solution, filtered and recrystallised from a mixture of EtOH and DMSO by addition of water. The crystals were filtered, washed with water and dried. The filtrate was diluted with water until cloudy, heated to solution and cooled to give addtional product. Further recrystallisation yielded 3-N-methylcarbamoylthioxanthene-9-one 10,10-dioxide, m.p. 223°–225° C.; TLC on silica gel ($CHCl_3$:acetone/9:1) one spot $R_f$ 0.49.

Analysis: calc. for $C_{15}H_{11}NO_4S$; C, 59.79; H, 3.68; N, 4.65. Found C, 59.74; H, 3.71; N, 4.62.

EXAMPLE 2

3-(2-Imidazolin-2-yl)thioxanthen-9-one 10,10-dioxide (Compound A)

To 13.5 g (0.05 mol) of 3-cyanothioxanthen-9-one 10,10-dioxide was added ethylenediamine, 6.0 g (0.1 mol), and sodium methoxide, 0.5 g (0.01 mol), in 100 ml methanol and the mixture was heated at reflux for 3 days. The reaction mixture was filtered hot and the solid was washed with two 50 ml portions of methanol. The crude product was recrystallized from ethanol to yield 3-(2-imidazolin-2-yl)thioxanthen-9-one 10,10-dioxide, 11.0 g, as bright orange crystals, m.p. 241°–242° C.

Analysis Calc. for $C_{16}H_{12}N_2O_3S$; C, 61.52; H, 3.87; N, 8.97. Found: C, 61.52; H, 3.78; N, 8.78.

EXAMPLE 3–6

The following compounds were prepared by the procedure recited in Example 2 with appropriate cyano (nitrile) starting materials prepared according to the methods described in the Hodson and Batchelor specifications.

3. 6-(2-Imidazolin-2-yl)-2-methylthioxanthen-9-one 10,10-dioxide (Compound F), m.p. 285°–287° C.
4. 6-(2-Imidazolin-2-yl)-2-propylthioxanthen-9-one 10,10-dioxide (Compound G), m.p. 200° C.
5. 6-(2-Imidazolin-2-yl)-2-isopropylthioxanthen-9-one 10,10-dioxide (Compound H), m.p. 202° C.
6. 2-Chloro-6-(2-imidazolin-2-yl)thioxanthen-9-one 10,10-dioxide (Compound P), m.p. 250°–252° C.

EXAMPLE 7

6-(2-Imidazolin-2-yl)-2-methoxythioxanthen-9-one 10,10-dioxide (Compound B)

(a) 7-Fluoro-9-oxo-3-thioxanthenecarboxylic acid

The method described in the Hodson and Batchelor specifications was used in condensing 4-fluorothiophenol, 19.2 g (0.15 mol), with 2,4-dicyanonitrobenzene, 26.0 g (0.15 mol), in DMF in the presence of NaH to give 35 g of 2,4-dicyano-4′-fluorodiphenylsulfide. This sulfide, 34 g (0.13 mole), was heated at reflux in a KOH solution to hydrolyze the cyano groups to the corresponding carboxylic acid groups. The resulting diacid compound was cyclized in $H_2SO_4$ by heating at 80° C. for an hour and the reaction mixture was poured into ice water to precipitate 7-fluoro-9-oxo-3-thioxanthenecarboxylic acid as yellow crystals. This material was collected, washed and dried to yield 22.2 g, m.p. 352° C.

Analysis: calc. for $C_{14}H_7FO_3S$; C, 61.31; H, 2.57. Found: C, 61.05; H, 2.59.

(b) 7-Fluoro-9-oxo-3-thioxanthene carboxylic acid-10,10-dioxide

To 256.78 g (0.936 mol) of 7-fluoro-9-oxo-3-thioxanthene carboxylic acid in 4.8 L of glacial acetic acid was added 528 ml of 30% $H_2O_2$ at 75° C. The mixture was refluxed 10 minutes, then an additional 125 ml of $H_2O_2$ was added to the mixture, and refluxing was continued for 10 minutes. The reaction mixture was diluted with $H_2O$ (2 L), chilled to 10° C. and filtered. The solid was washed with 3×1 L of $H_2O$ and dried, m.p., 325°–330° C.; TLC on silica gel (butanol:acetic acid:water/5:4:1), $R_f$=0.69.

Analysis: calc. for $C_{14}H_7FO_5S$; C, 54.91; H, 2.30; S, 10.47. Found: C, 54.96; H, 2.34; S, 10.47.

(c) 7-Methoxy-9-oxothioxanthene-3-carboxylic acid 10,10-dioxide

Fifteen g (0.049 mol) of 7-fluoro-9-oxo-3-thioxanthene carboxylic acid 10,10-dioxide was dissolved in HMPA (hexamethylphosphoramide) (300 ml) and to this was added sodium methoxide, 6.75 g (0.13 mol), in HMPA, 225 ml.

The solution was stirred at 150° C. for 2–5 hr and was then poured into ice water, 1 L. The mixture was acidfied with conc. HCl, diluted to 1.5 L and cooled overnight. The precipitate was filtered, dried and recrystalised from a mixture of EtOH, DMSO and $H_2O$ to yield 6.4 g of 7-methoxy-9-oxothioxanthene-3-carboxylic acid 10,10-dioxide as an orange powder, m.p 300°–305° C.; TLC on silica gel (ethanol), $R_f$=0.74.

Analysis: calc. for $C_{15}H_{10}O_6S$; C, 56.60; H, 3.17. Found: C, 56.63; H, 3.21.

(d) 3-Cyano-7-methoxy-9-oxothioxanthene 10,10-dioxide

A solution of 7-methoxy-9-oxothioxanthene-3-carboxylic acid 10,10-dioxide, 6 g (0.019 mol), in thionyl chloride, 35 ml, was refluxed for 2.75 hr. The thionyl chloride was removed under reduced pressure, and the residue was stirred in concentrated NH$_4$OH for 1.5 hr. The precipitate was filtered, washed with water and dried to afford the amide, 5.8 g. The amide was added to a cooled (0°) solution of thionyl chloride 11 ml in DMF 36 ml, and the mixture was stirred at 0°–10° C. for 1 hr, then at room temperature for 1.5 hr. The mixture was poured into ice water (200 ml) and the resultant solid was filtered and dried (5.2 g); TLC on silica gel (hexane/ethylacetate:7/2), $R_f$=0.59.

(e) 6-(2-Imidazolin-2-yl)-2-methoxythioxanthen-9-one-10,10-dioxide

To 5.0 g (0.017 mol) of 3-cyano-7-methoxythioxanthen-9-one 10,10-dioxide was added ethylenediamine, 10.8 g (0.18 mol), and sodium methoxide, (0.098 g, 0.002 mol), in methanol, 70 ml, and the mixture was refluxed for 70.5 hr. The mixture was then poured into ice water, 400 ml, and the precipitate was filtered and washed with water then was recrystallized from ethanol, DMSO and H$_2$O to provide 1.1 g of 6-(2-imidazolin-2-yl)-2-methoxythioxanthen-9-one-10,10-dioxide with m.p. 220°–224° C.; TLC on silica gel (ethanol), $R_f$=0.44.

Analysis: calc. for C$_{17}$H$_{14}$N$_2$O$_4$S; C, 59.64; H, 4.12; N, 8.18. Found: C, 59.83; H, 4.29; or 8.36.

EXAMPLES 8 AND 9

The compounds of these two examples were prepared from 7-fluoro-9-oxo-3-thioxanthene carboxylic acid 10,10-dioxide by the procedure of example 6.

8. 2-Ethoxy-6-(2-imidazolin-2-yl)thioxanthen-9-one, 10,10-dioxide (Compound C), m.p. 278°–279° C. (dec).

9. 6-(2-Imidazolin-2-yl)-2-propoxythioxanthen-9-one 10,10-dioxide (Compound D), m.p. p. 157°–160° C. (dec).

EXAMPLE 10

6-(2-Imidazolin-2-yl)-2-fluorothioxanthene-9-one 10,10-dioxide (Compound E)

(a) 7-Fluoro-9-oxothioxanthene-3-carboxamide-10,10-dioxide

A mixture of 7-fluoro-9-oxo-3-thioxanthene carboxylic acid 10,10-dioxide (see example 6), 34.0 g (0.11 mol), and thionyl chloride, 130.9 g (1.10 mol), was heated at reflux for 2.0 hr. Dimethyl formamide, 1 ml, was added to the mixture, giving a solution which was heated at reflux overnight. The reaction was cooled, and a yellow crystalline solid, 27.85 g, was collected and washed with ether. A portion of the acid chloride, 5.0 g, was placed in concentrated NH$_4$OH, 50 mL, and heated on a steam bath for 0.5 hr. The solid was filtered and washed with H$_2$O and acetone to give 3.82 g of the amide. A small amount of the amide was recrystallized from DMF:MeOH/75:25 to provide 0.3 g of a light yellow crystalline 7-fluoro-9-oxothioxanthene-3-carboxamide 10,10-dioxide, m.p. 307°–310° C. TLC (CHCl$_3$/MeOH/9/1) $R_f$=0.45.

Analysis: calc. for C$_{14}$H$_8$FNO$_4$S; C, 55.08; H, 2.64; N, 4.59; S, 10.50. Found: C, 55.13; H, 2.66; N, 4.61; S, 10.57.

(b) 6-Cyano-2-fluorothioxanthene-9-one 10,10-dioxide

Thionyl chloride (75 g) was cooled to 5° C. and DMF (150 ml) was added dropwise and the temperature was maintained below 10° C. The amide prepared in (a) supra, 19.1 g, (0.05 mol) was added and the mixture was allowed to warm to room temperature and was stirred for 2 hr. The mixture was poured onto 1 L of ice and was filtered. The solid was washed with H$_2$O, 2×300 ml and dried. The nitrile was dissolved in hot acetic acid (800 ml), treated with charcoal and filtered through a celite bed. The solution was cooled, and the crystals were collected by filtration and dried in vacuo to give 14.48 g of 6-cyano-2-fluorothioxanthene-9-one 10,10-dioxide, m.p.=260°–262°0 C.; TLC on silica gel (butanol:acetic acid:H$_2$O/5:4:1), $R_f$=0.82.

Analysis: calc. for C$_{14}$H$_6$FNO$_3$S; C, 58.54; H, 2.11; N, 4.88; S, 11.16. Found: C, 58.61; H, 2.14; N, 4.81; S, 11.20.

(c) 6-(2-Imidazolin-2-yl)-2-fluorothioxanthen-9-one 10,10-dioxide

A mixture of 6-cyano-2-fluorothioxanthene-9-one 10,10-dioxide, 5.2 g (0.02 mol), ethylenediamine, 1.2 g (0.02 mol), and sodium methoxide, 0.08 g (0.0015 mol), in methanol, 76 ml, was refluxed for 4 days. Additional ethylenediamine, 1.2 g (0.02 mol), was added and reflux continued for 5 days. The mixture was poured into ice and the precipitate was filtered, dried and recrystallised from ethanol, DMSO and H$_2$O; affording 2.6 g of 6-(2-imidazolin-2-yl)-2-fluorothioxanthen-9-one 10,10-dioxide, m.p. 248°–249° C.; TLC on silica gel (triethylamine; ethanol; hexane/1:1:2), $R_f$=0.8.

Analysis: calc. for C$_{16}$H$_{11}$FN$_2$O$_3$S; C, 58.18; H, 3.36; N, 8.48. Found: C, 57.88; H, 3.49; N, 8.60.

EXAMPLE 11

2-Dimethylamino-6-(2-imidazolin-2-yl)thioxanthen-9-one 10,10-dioxide dihydrochloride (Compound J)

(a) 6 Cyano-2-dimethylamino-thioxanthen-9-one 10,10-dioxide

To 30 g (0.1 mol) of 7-fluoro-9-oxothioxanthene-3-carbonitrile 10,10-dioxide (this compound is prepared by the method of example 6d, supra), was added anhydrous dimethylamine, 400 ml. The mixture was stirred at room temperature until the excess amine had evaporated. The residue was collected and washed with ether to give 39.3 g of the crude product. A small amount of 6 Cyano-2-dimethylaminothioxanthen-9-one 10,10-dioxide was recrystallized from DMSO to give 2.4 g of red crystals with m.p. 291°–294° C.; TLC on silica gel (hexane:EtOAc/3:2), $R_f$=0.45.

Analysis: calc. for C$_{16}$H$_{12}$N$_2$O$_3$S; 61.53; H, 3.87; N, 8.97. Found: C, 61.49; H, 3.92; N, 8.93.

(b) 2-Dimethylamino-6-(2-imidazolin-2-yl)thioxanthen-9-one 10,10-dioxide dihydrochloride A mixture of 6-cyano-2-dimethylaminothioxanthen-9-one 10,10-dioxide, 2.0 g (0.006 mol), ethylenediamine, 3 g, 0.05 mol, and sodium methoxide, 0.1 g (0.002 mol) in methanol, 30 ml, was refluxed for 48 hr. The mixture was poured into H$_2$O and the resultant precipitate was dissolved in boiling in 1N HCl. This solution was cooled and the dihydrochloride salt was filtered and recrystallized from 95% ethanol to yield 2-dimethylamino-6-(2-imidazolin-2-yl)thioxanthen-9-one 10,10-dioxide dihydrochloride 0.3 g with m.p. 330°–335° C. (dec); TLC on silica gel (ethylacetate:ethanol:acetic acid/80:15:5), $R_f$=0.4.

Analysis calc. for C$_{18}$H$_{17}$N$_3$O$_3$S.2HCl; C, 50.47; H, 4.47; N, 9.81. Found: C, 50.25; H, 4.37; N, 9.70.

EXAMPLES 12–17

The compounds in the following examples were prepared by the method of Example 10, supra, substituting the appropriate amino compound in place of dimethylamine.

12. 2-Ethylamino-6-(2-imidazolin-2-yl)thioxanthen-9-one 10,10-dioxide hydrochloride (Compound I), m.p. 284°–286° (dec.).
13. 6-(2-Imidazolin-2-yl)-2-(propylamino)thioxanthene-9-one 10,10-dioxide (Compound K), m.p. 105°–107° C. (dec).
14. 2-(N-Ethylmethylamino)-6-(2-imidazolin-2-yl)-thioxanthen-9-one 10,10-dioxide hydrochloride (Compound L), m.p. above 300° C.
15. 2-Allylamino-6-(2-imidazolin-2-yl)-thioxanthen-9-one 10,10-dioxide (Compound M), m.p. 176.5°–177.5° C.
16. 6-(2-Imidazolin-2-yl)-2-morpholinothioxanthen-9-one 10,10-dioxide isethionate (Compound O) m.p. 186°–188° C.
17. 2-(2-Aminoethylamino)-6-(2-imidazolin-2-yl)thioxanthen-9-one 10,10-dioxide dihydrochloride (Compound N) m.p. 278°–282° C. (dec).

EXAMPLE 18

3-Ethylcarbamoyl-7-propoxythioxanthen-9-one 10,10-dioxide (Compound Q)

The title compound was prepared by the method of Example 7c followed by the reference method of Example 1, m.p. 183°–185° C.

EXAMPLE 19

7-Isopropyl-3-methylcarbamoylthioxanthen-9-one 10,10-dioxide (Compound R)

The title compound was prepared by the reference method of Example 1 from the corresponding acid prepared by the methods described in the Hodson and Batchelor specifications, m.p. 2–3°–205° C.

In the following formulation examples, 'active ingredient' means a compound of formula (I) as hereinbefore defined or a physiologically acceptable salt thereof. When referring to salts, weights are expressed in terms of weight of the anion.

EXAMPLE 20

Pharmaceutical Formulation

Example A 100 mg Compression Coated Tablet

|  | Ingredients | Amount Per Tablet |
|---|---|---|
| Core | Active Ingredient | 100 mg |
|  | Starch | 25 mg |
|  | Magnesium Stearate | 2 mg |
| Coating | Lactose | 320 mg |
|  | Starch | 50 mg |
|  | Gelatin | 6 mg |
|  | Magnesium Stearate | 4 mg |

The active ingredient and starch are granulated with water and dried. Magnesium stearate is added to the dried granules. Lactose and starch are granulated with a 10% w/v aqueous solution of gelatin and dried. Magnesium stearate is added to the dried granules. The granulated core is compressed with the granulated coating in a conventional compression molding machine.

Example B 200 mg Capsule

| Ingredients | Amount Per Capsule |
|---|---|
| Active Ingredient | 200 mg |
| Lactose | 200 mg |
| Talc | 40 mg |

The active ingredient, lactose and talc are brought into intimate admixture with one another and 440 mg of the resultant mixture is introduced into a size 0 hard gelatin capsule.

Example C 100 mg Capsule

| Ingredients | Amount Per Capsule |
|---|---|
| Active Ingredient | 100 mg |
| Lactose | 100 mg |
| Corn Starch | 100 mg |
| Magnesium Stearate | 10 mg |

The ingredients are mixed together until homogeneous and 310 mg of the resulting mixture filled into each hard gelatin capsule.

Example D 500 mg Tablet

| Ingredients | Amount Per Tablet |
|---|---|
| Active Ingredient | 500 mg |
| Corn Starch | 100 mg |
| Microcrystalline Cellulose | 75 mg |
| Magnesium Stearate | 10 mg |
| Granulated polyvinylpyrrolidone 10% w/v in 50% w/v aqueous ethanol | 5 mg |

The active ingredient, corn starch and microcrystalline cellulose are mixed together, and granulated with the alcoholic polyvinylpyrrolidone. The resulting granules are dried, and compressed to produce tablets, each tablet having a weight approximately 690 mg. The active ingredient is dissolved in the bulk of the Water and then made up to volume and sterilised by filtration. The resulting solution is distributed into ampoules under aseptic conditions.

Example E

Suppository

| Ingredient | Amount Per Suppository |
|---|---|
| Active Ingredient | 200 mg |
| Suppository Base | 1.8 mg |

The active ingredient in fine powder form was dispersed into a little of the molten Suppository Base at 50° C. The dispersion is incorporated into the bulk of the base at the same temperature, allowed to cool at 42°–45° C., poured into suitable 2 g suppository molds and allowed to set at 15°–20° C. suppository bases are Massa Esterinum C and Witten H Suppository Compound.

Example F

Dispersible Tablet

| Ingredient | Amount Per Tablet |
| --- | --- |
| Active Ingredient | 200 mg |
| Corn Starch | 40 mg |
| Primojel (Trade name: sodium starch glycollate (125 # m powder)) | 50 mg |
| Dicalcium Phosphate Dihydrate | 50 mg |
| Sodium Carboxymethyl Cellulose | 2 mg |
| Sodium Saccharin | 5 mg |
| Microcrystalline Cellulose | 50 mg |
| Magnesium Stearate | 3 mg |

The active ingredient, half of the corn starch, the primojel and dicalcium phosphate are mixed together and then granulated with a solution of sodium carboxymethyl cellulose, and sodium saccharin in a suitable volume of 50% ethyl alcohol. The granules were dried, the remaining corn starch, the microcrystalline cellulose and the magnesium stearate are blended-in and the resulting mixture compressed into tablets.

EXAMPLE 21

In Vitro Inhibition of Monoamine Oxidase-A

MAO was assayed with [$^3$H]. serotonin (0.2 mM, 5 Ci/mol) and [$^{14}$C] β-phenethylamine (10 μM, 3 Ci/mol) as substrates in a double-label assay (White and Glassman, J. Neurochem 29:987–97 1977).

MAO activity was determined in the absence and presence of the compound under test at each substrate concentration. Table I below lists $I_{50}$ values found for certain of the preferred compounds of formula (I).

TABLE I

| Inhibition of MAO-A (In Vitro) | |
| --- | --- |
| Compound | $I_{50}$ (× $10^{-6}$ M) |
| H | 0.05 |
| J | 0.02 |
| L | 0.04 |
| O | 0.012 |
| E | 0.20 |

What is claimed is:

1. A method of treating depression in a mammal identified as being in need of such treatment, comprising administration to said mammal of an effective depression treatment amount of a compound of formula (I)

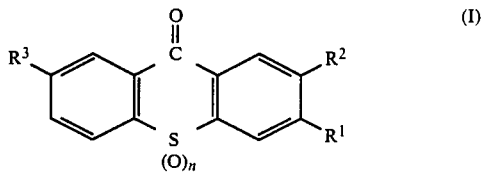

n is 0, 1 or 2;

one of $R^1$ and $R^2$ is hydrogen and the other is selected from carbamoyl, N-$C_{1-4}$alkylcarbamoyl, N,N-di-$C_{1-4}$alkylcarbamoyl, carbamimidoyl, $N^1$-$C_{1-4}$alkylcarbamimidoyl, $N^2$-$C_{1-4}$alkylcarbamimidoyl, $N^1$-$C_{1-4}$alkyl-$N^2$-$C_{1-4}$alkylcarbamimidoyl, $N^1$,$N^1$-di-$C_{1-4}$alkylcarbamimidoyl, $N^1$,$N^1$-di-$C_{1-4}$alkyl-$N^2$-$C_{1-4}$alkylcarbimidoyl, and imidazolin-2-yl (optionally substituted by one or more $C_{1-4}$alkyl groups); and $R^3$ is selected from hydrogen, saturated and unsaturated aliphatic hydrocarbon moieties containing from 1 to 4 carbon atoms, groups $OR^4$ (where $R^4$ is selected from hydrogen and saturated and unsaturated aliphatic hydrocarbon moieties containing from 1 to 4 carbon atoms), halo, groups of formula —$NR^5R^6$ (where $R^5$ and $R^6$ are independently selected from hydrogen, $C_{1-4}$alkyl and hydroxy $C_{1-4}$alkyl, provided that the total number of carbon atoms in $R^5$ and $R^6$ does not exceed 4), amino-$C_{1-4}$alkylamino and morpholino; provided that when n is 2 and $R^2$ is hydrogen, then $R^1$ is not carbamoyl when $R^3$ is hydrogen or methyl; and $R^1$ is not N-methylcarbamoyl when $R^3$ is hydrogen; or a physiologically acceptable salt thereof.

2. The method of claim 1 in which the compound 3-carboxythioxanthen-9-one 10,10-dioxide or a physiologically acceptable salt thereof is administered.

* * * * *